US012797432B2

(12) United States Patent
Shah et al.

(10) Patent No.: US 12,797,432 B2
(45) Date of Patent: Nov. 17, 2026

(54) MODIFIED RELEASE FORMULATION COMPRISING WITHANOLIDES

(71) Applicant: NUTRIVENTIA PRIVATE LIMITED, Mumbai (IN)

(72) Inventors: Vishal Shah, Mumbai (IN); Rajat Shah, Mumbai (IN); Shajahan Abdul, Madurai (IN)

(73) Assignee: NUTRIVENTIA PRIVATE LIMITED, Mumbai (IN)

( * ) Notice: Subject to any disclaimer, the term of this patent is extended or adjusted under 35 U.S.C. 154(b) by 228 days.

(21) Appl. No.: 18/260,956

(22) PCT Filed: Aug. 17, 2022

(86) PCT No.: PCT/IB2022/057698

§ 371 (c)(1),
(2) Date: Jul. 11, 2023

(87) PCT Pub. No.: WO2023/021434

PCT Pub. Date: Feb. 23, 2023

(65) Prior Publication Data

US 2024/0058412 A1 Feb. 22, 2024

(30) Foreign Application Priority Data

Aug. 20, 2021 (IN) ............................ 202121037821

(51) Int. Cl.
*A61K 36/81* (2006.01)
*A61K 9/16* (2006.01)
*A61P 25/22* (2006.01)
*A61P 25/24* (2006.01)

(52) U.S. Cl.
CPC ............ *A61K 36/81* (2013.01); *A61K 9/1611* (2013.01); *A61K 9/1617* (2013.01); *A61K 9/1652* (2013.01); *A61P 25/22* (2018.01); *A61P 25/24* (2018.01); *A61K 2121/00* (2013.01)

(58) Field of Classification Search
None
See application file for complete search history.

(56) References Cited

U.S. PATENT DOCUMENTS

| | | | |
|---|---|---|---|
| 8,858,995 | B2 | 10/2014 | Gupta et al. |
| 9,987,323 | B2 | 6/2018 | Antony |
| 2008/0305096 | A1 | 12/2008 | Verdegem et al. |
| 2016/0158152 | A1 | 6/2016 | Trivedi et al. |
| 2017/0326195 | A1 | 11/2017 | Antony |

FOREIGN PATENT DOCUMENTS

| | | | |
|---|---|---|---|
| IN | 202021006119 | * | 8/2021 |
| WO | 2007014334 | A2 | 2/2007 |
| WO | 2015008301 | A1 | 1/2015 |
| WO | 2020079712 | A1 | 4/2020 |
| WO | 2020144591 | A2 | 7/2020 |

OTHER PUBLICATIONS

Database TKDL, Anonymous : "Zaroor-e-Asgand; 200 years," XP093038652, Retrieved from TKDL.
Patil et al., Journal of Pharmaceutical and Biomedical Analysis 80 (2013) 203 212.
Dahikar et al., International Journal of Pharmacognosy and Phytochemical Research 2012-13, 4(4):195-198.

* cited by examiner

*Primary Examiner* — Michael V Meller
(74) *Attorney, Agent, or Firm* — Blank Rome LLP

(57) ABSTRACT

The invention describes a modified release formulation comprising 2 to 10% withanolides, obtained from root powder of *Withania somnifera*. The formulation is comprised of at least one pH independent release controlling agent or the combination thereof. The invention also provides a process for preparation of modified release composition; wherein Ashwagandha root powder enriched with withanolides is uniformly dispersed and embedded throughout the matrix of at least one pH independent release controlling agent. The granules can be conveniently formulated in suitable compressible dosage forms, filled in sachets or capsules for oral administration. The formulation may release more than 75% of withanolides over a period of 6 to 12 hours. The modified release formulation may be useful for maintaining significant concentration of withanolides in blood plasma over extended time and can be administered to the subjects in need thereof for stress management, cognitive benefits and improving overall mental well-being.

8 Claims, No Drawings

MODIFIED RELEASE FORMULATION COMPRISING WITHANOLIDES

FIELD OF INVENTION

The invention relates to a modified release formulation comprising withanolides. Particularly, the formulation as described herein, may be comprised of about 2 to 10% of withanolides obtained from roots of *Withania somnifera*. The formulation may be comprised of at least one pH independent release controlling agent. The invention also provides process for preparation of modified release composition; wherein root powder enriched in withanolides is uniformly dispersed and embedded throughout the matrix of at least one pH independent release controlling agent and at least one excipient, acceptable in nutraceutical and/or pharmaceutical industry. The granules are smooth and uniform in nature, which can be conveniently formulated in suitable compressible dosage forms, filled in sachets or capsules for oral administration. The process of preparation is simple, economic and makes use of commonly available industrial equipment. The formulation may release more than 75% of withanolides over a period of 6 to 12 hours. The modified release formulation is useful for maintaining significant concentration of withanolides in blood plasma over extended time. The formulation is safe and can be administered to the subjects in need thereof for stress management, improvement in cognitive abilities, memory, quality of sleep, and for overall improved mental well-being.

BACKGROUND OF THE INVENTION

Withanolides are the major group of chemical constituents reported in *Withania somnifera*, (commonly also called as Ashwagandha or Indian ginseng). The chemical investigations of the roots and leaves of *Withania somnifera* resulted in the isolation and characterization of several withanolides (Matsuda, M., et al., Bioorg. Med. Chem. 9, 1499-1507 (2001)). Withanolides are a group of naturally occurring C-28 steroidal lactones with an intact ergostane structure, in which C-22 and C-26 are oxidized to form a six-membered lactone ring. The fruits of this plant are tiny orange berries and reported to contain saturated and unsaturated fatty acids. However, leaves and fruits are not fully investigated for biological activities. Ashwagandha is an evergreen shrub native to the Indian sub-continent. Withanolides from Ashwagandha have been studied for their anti-inflammatory, antitumor, immunomodulating activities and for the protection against $CCl_4$-induced hepatotoxicity. Ashwagandha roots have been also used in ancient Indian medicine for treating sleep disorders, arthritis, rheumatism, syphilis and chronic fatigue. Ashwagandha is one of the herbs that purportedly promotes youth and longevity and alleviates suffering. It is thought to be especially rejuvenative for men; to strengthen bone marrow, muscle, and semen; it also supports for enhancing serum testosterone levels in addition to long life and youthful vitality. However, it also is believed to be quite helpful to the elderly by providing energy and relieving pain, inflammation, and nervous debility. The roots are also used for treating constipation, asthma, hypertension and tuberculosis. Efficacy of ashwagandha extracts and isolated constituents has been reported in experimental models of neurodegenerative disorders such as Alzheimer's disease (AD) and Parkinson's disease (PD), which are associated with the disruption of neural networks and premature death of neurons.

In modern society, stress is a common problem faced in day-to-day life from different sources like job, family problems, pollution, noise and the like. Stress and an inability to perform at a required level of cognition can induce anxiety. Cognitive deficits are related to impaired everyday functioning in stressed healthy individuals. Continuous exposure to the stressful life events affects the psychological wellbeing of humans. Altered psychological wellbeing results in conditions like depression and anxiety. The critical goals of the cognitive enhancement are to improve everyday functioning in multiple domains. Traditional systems of complementary medicine, such as Ayurveda has used herbal therapies to aid memory and cognition for thousands of years. Although Ashwagandha is classified as a Rasayana and being used since centuries in multiple therapeutic areas including anxiety and stress, memory and cognition, its typical dosage is twice or thrice a day. This often leads to patient non-compliance especially when administered for a long duration as a health supplement for use in stress management, sleep disorders or in chronic conditions like rheumatism, hypertension or fatigue conditions.

Prior are search indicates very few efforts for designing the controlled or delayed-release formulations of actives by using various approaches.

U.S. Pat. No. 9,987,323 relates to compositions of Ashwagandha extract enriched with withanolide glycosides and saponins after removing alkaloids, withanolide aglycones and oligosaccharides. The disclosure also provides a method of improving bioactivity of withanolide glycosides at lower doses, by the administration of an enteric coated formulation of extract of Ashwagandha to humans. The enteric coating protects the composition from hydrolysis in the acidic environment of the stomach to release the withanolide glycoside in neutral/alkaline pH in gastrointestinal tract (GIT) thus enhancing the absorption.

US 20080305096 describes a composition based on use of soluble fibres for controlling release of the active. The composition is comprised of biological active substance and one or more soluble fibres, selected from guar gum, gum Arabic, locust bean gum, pectin, oat fibre, beta glucan, psyllium, gum acacia, xanthan gum, inulin, fructo-oligosaccharides (FOS), carrageenan, which may be mixed with gas generating mineral salts. However, the application does not provide any further information or exemplification to showcase specific formulation containing any of the listed actives.

WO 2020144591 describes an enteric coated delivery system for *Withania somnifera*, wherein a solid bead core is coated with a layer of *Withania somnifera* and which further comprises of a protective enteric layer to protect the active layer from the acidic environment of the stomach, wherein the protective layer comprises of methacrylic acid copolymers, cellulose acetate phthalate, polyvinyl acetate phthalate, shellac, cellulose acetate trimellitate, hydroxypropyl methylcellulose phthalate, alginate, pea starch, beta-acacia and combination thereof.

U.S. Pat. No. 8,858,995 relates to polymeric controlled release composition comprising a phytochemical incorporated in a polymeric matrix which is further coated with a polymeric coating of polycaprolactone. The phytochemical component discloses withaferin A as one of the examples in its composition and wherein the polymeric matrix comprises of polycaprolactone, cyclodextrin, and polyethylene glycol and the composition is mainly used for treatment of chronic disease like cancer.

US 20160158152 relates to a pharmaceutical composition in the form of liposomal vesicles for prevention and treatment of diminution of bone, which is comprised of a compound selected from the group consisting of Withaferin A, Withanolide A, and Withanone and pharmaceutically acceptable excipients selected from the group comprising lipids, and polymers. in combination with non-ionic surfactant. The lipids are selected from the group consisting of soya phosphatidylcholine, di-stearoyl phosphatidylcholine, di-stearoylphosphatidyl glycerol, and cholesterol. The composition is prepared by contacting the active and lipids in a solvent to form film, which is then converted into multilayered liposomes.

Dahikar et al. (*International Journal of Pharmacognosy and Phytochemical Research* 2012-13; 4(4); 195-198) investigated the disposition kinetics of *Withania somnifera* (Ashwagandha) after single dose administration of 500 mg/kg, orally in six non-descript healthy buffalo calves. The researchers noted that the mean therapeutic concentration of *Withania somnifera* was maintained from 10 min to 3 h in plasma of healthy buffalo calves, whereas the mean elimination half-life of *Withania somnifera* was observed to be 0.92±0.032 h. The drug was not detectable in any of six animals after 4 h.

Patil et al (*Journal of Pharmaceutical and Biomedical Analysis* 80 (2013) 203-212) developed and validated selective and rapid high performance liquid chromatography-tandem mass spectrometry (HPLC-MS/MS) method for simultaneous determination of withaferin-A and withanolide-A in mice plasma. The validated method was successfully applied for the determination of WA and WLD after oral administration of *Withania somnifera* extract at a dose of 1000 mg/kg. The half-life of 59.92±15.90 min and 45.22±9.95 min for withaferin-A and withanolide-A respectively were observed.

Both the studies reported a very short elimination half-life of withanolides, indicating need of frequent administration of the active in a day, for achieving the required therapeutic effect. However, this may result into the patient non-compliance. Accordingly, there remains a need in the art for designing formulations for the delivery of compounds like withanolides having longer elimination half-life and can exhibit the prolonged release of active over extended time of 6 to 24 hours. More specifically, there remains a need in the art for designing the formulations which can be administered once a day, for achieving the desired effect of the active, thus avoiding frequent administration of the medicament. Such formulations would deliver entire spectrum of withanolides over prolonged time in a modified manner. This would be useful to achieve and maintain desired blood plasma levels of the active throughout the day, so that these can be efficiently utilized in subjects in need thereof for intended health benefits such as stress management, improvement in cognitive effects, memory and sleep.

SUMMARY OF THE INVENTION

Developing modified release dosage form comprising total withanolides, which will provide continuous supply of required amounts of the active moiety throughout the day, is an unmet need identified by the team of researchers of the present invention. Such formulations should also ensure availability of the active form of withanolides in the body for absorption, to maintain significant concentration in the blood plasma for prolonged time.

The researchers of the present invention have surprisingly found that optimum selection of one or more pH independent release controlling excipients has resulted in the formulation which exhibits modified or sustained release of withanolides over a period of 6 to 12 hours. The formulation is comprised of 2 to 10% of total withanolides and it is granular in nature, which can be compressed in suitable dosage forms, filled in capsules or sachets for convenient oral administration to the subjects for maintaining significant concentration of withanolides in body over 6 to 24 hours.

The invention also relates to the process for preparation of modified release formulation comprising total withanolides obtained from Ashwagandha root by process of aqueous alcoholic extraction, wherein the active may be uniformly dispersed and embedded in 30 to 70% by weight of at least one pH independent release controlling agent and at least one excipient which is acceptable in nutraceutical or pharmaceutical industry to get free flowing matrix granules. The granular composition as described herein ranges in size from 100 to 1000 microns and the granules are taste masked, smooth, and uniform in nature, which can be conveniently formulated in desired dosage form for oral administration of modified release formulations. The composition may release more than 75% of withanolides over a period of 6 to 12 hours.

The modified release formulation may be useful for maintaining significant concentration of withanolides in blood plasma over extended time and can be administered to the subjects in need thereof for stress management, cognitive benefits, mental health, improvement in quality of sleep and for achieving overall improved well-being.

None of the prior art references describe modified release formulation comprising 2 to 10% of withanolides, which is comprised of at least one pH independent release controlling agent or the combination thereof, and exhibits modified release of more than 75% of withanolides over 6 to 12 hours, thus providing significant concentration of the active in blood plasma over extended time, in order to manage conditions like stress induced cognitive disorders, anxiety, quality of sleep and to achieve overall improved well-being.

OBJECTS OF THE INVENTION

Main objective of the invention is to provide a modified release formulation comprising withanolides and a process for preparation of said formulation.

Another objective of the invention is to provide modified release formulation comprising total withanolides, which is obtained from roots of *Withania somnifera* (Ashwagandha) by process of aqueous alcoholic extraction.

Another important objective of the invention is to provide the modified release formulation comprised of 2 to 10% of total withanolides, including withanolide glycosides, withanolide aglycones, and withaferin A. This formulation exhibits its modified release of more than 75% of withanolides in vitro over 6 to 12 hours, thus resulting into significant concentration of the active in the blood plasma over extended time.

Another objective of the invention is to provide modified release formulation comprising Ashwagandha root powder enriched in withanolides, at least one pH independent release controlling agent or the combination thereof, and at least one excipient, which is acceptable in nutraceutical and pharmaceutical industry.

Other objective of the invention is to provide modified release formulation comprising about 20 to 70% by weight of Ashwagandha root powder in combination with about 30 to 70% by weight of pH independent release controlling agent and about 1 to 10% by weight of at least one more excipient, which acts as a processing aid for preparation of granular composition.

Important objective of the invention is to provide modified release withanolide formulation comprising at least one pH independent release controlling agent or the combination thereof, selected from the group of, but not limited to cellulose and cellulose derivatives, vinyl pyrrolidone-vinyl acetate copolymer, polyvinyl alcohol, starch and starch derivatives, gums, fatty acids, long chain alcohols, fats, lipids, waxes, oils or the combination thereof.

The pH independent release controlling agent may be hydrophilic or hydrophobic in nature, and it may be used either alone or in combination thereof, as per the scope of this invention to obtain modified release formulation.

The objective of the invention is also to provide modified release withanolide formulation comprising at least one pH independent release controlling agent, selected from the group of cellulose derivatives such as hydroxypropylmethyl cellulose (HPMC), hydroxypropyl cellulose (HPC), ethylcellulose, carboxymethylcellulose (CMC), sodium CMC, potassium CMC, calcium CMC, methylcellulose, hydroxyethyl cellulose (HEC), starch and starch derivatives, gums like xanthan gum, guar gum, acacia, locust bean gum, alginates, or mixtures thereof.

Another objective of the present invention is to provide modified release withanolide formulation, comprising at least one pH independent release controlling agent, selected from the group of saturated fatty acids having 12 to 28 carbons, such as stearic acid, fatty alcohols having from 16 to 44 carbons, cetyl alcohol, pegylated fatty acids, glycerol fatty acid esters, monoglycerides, diglycerides, triglycerides, derivatives of mono-diglycerides, glyceryl behenate, glyceryl monostearate, glyceryl palmitostearate, pegylated vegetable oils, partially hydrogenated oils of soy, cottonseed, palm, sunflower, castor oil, sorbitan esters, polyoxyethylene sorbitan esters, propylene glycol mono- or diesters, phospholipids, phosphatides, cerebrosides, gangliosides, cephalins, lipids, glycolipids, sulfatides, sugar esters, sugar ethers, sucrose esters, sterols, polyglycerol esters, glycerolipid, phosphatic acid, phosphatidylethanolamine, phosphatidylcholine, phosphatidylserine, phosphatidylinositol or other glycerophospholipids, ceramide, sphingolipid, sterol, fat-soluble vitamin, prenol, saccharolipid, polyketide, their salts and esters and the combination thereof.

One important objective of the invention is to provide a process for preparation of modified release formulation, wherein the active may be dispersed uniformly and embedded in about 30 to 70% by weight of pH independent release controlling agent and about 1 to 10% by weight of at least one excipient. The resulting granules are taste masked, smooth and free flowing, which can be formulated in desired solid dosage forms.

The objective of the invention is to provide process for preparation of modified release formulation comprising 2 to 10% withanolides, which is simple, convenient and employs use of commonly used equipment, thus making it time and cost effective. The formulation can be suitably orally administered, for maintaining significant concentration of detectable amount of withanolides in the blood plasma over 6 to 24 hours.

Another important objective of the present invention is to provide a modified release formulation comprised of withanolides, obtained from root powder of Ashwagandha, which is safe for administration to the subjects in need thereof, for management of stress, improvement in cognitive abilities along with improvement in memory, sleep, and overall mental well-being.

DETAILED DESCRIPTION OF THE INVENTION

The invention relates to a modified release formulation, comprising withanolides obtained from roots of *Withania somnifera*, also called as Ashwagandha. The formulation may be comprised of at least one pH independent release controlling agent or the combination thereof, and at least one more excipient which is acceptable in nutraceutical and pharmaceutical industry. The invention also relates to the process for preparation, wherein Ashwagandha root powder enriched in withanolides, may be uniformly dispersed and embedded in matrix of at least one pH independent release controlling agent or the combination thereof; to get the granular formulation. The granules are smooth and free flowing and can be converted into compressible dosage forms like tablets, minitablets, caplets, pellets, and the like, or filled in sachets or capsules.

Continuous exposure to stressful life events is an established risk factor for the development of many psychological disorders in humans including major depression, anxiety and cognitive impairment. Chronic unpredictable stress (CUS) leads to cognitive deficit and anxiety-like behavior which is generally treated with antidepressant drugs. Thus the standard medical practice lacks the proper management of stress. Although Ashwagandha has shown beneficial effects on cognition enhancement, its short elimination half-life necessitates the frequent administration and results into non-compliance, thus making it difficult to achieve desired effect during long term administration. It would be thus desirable to design the formulation having modified release of the active over prolonged time, which will be useful to maintain the concentration of withanolides by avoiding rapid clearance from the system. The formulation as described herein is therefore designed as a modified release system, which may be useful for stress management and for conferring the cognitive benefits to the subjects in need thereof.

As per the important embodiment of the present invention, the formulation described herein employs withanolides (also synonymously called as total withanolides) obtained from roots of Ashwagandha. The withanolides may be obtained by treatment of Ashwagandha root powder with organic solvents.

As per one embodiment, the organic solvents used for the process, may be selected from but not limited to C1-C5 alcohols, like ethanol, methanol, n-butanol and mixtures thereof, C1-C7 hydrocarbons such as hexane; esters like ethyl acetate and mixtures thereof.

Ashwagandha root powder, as used in the present invention, is a dry powder which is light brown to dark brown in colour. Ashwagandha root powder is enriched with withanolides, comprised of withanolide glycoside, withanolide aglycones and withaferin A.

As per important embodiment of the present invention, Ashwagandha root powder is enriched with 8-20% of total withanolides, more particularly it is comprised of withanolide glycosides in the range of 3-15%, withanolide aglycones in the range of 2.5-8%, and withaferin-A in the range of 0.01-0.7%.

As per important embodiment of the invention, the formulation may be comprised of about 20 to 70% by weight of Ashwagandha (*Withania somnifera*) root powder, enriched in total withanolides.

As described herein, it was surprisingly observed that when withanolides obtained from Ashwagandha root powder were uniformly dispersed and embedded in a matrix of at least one pH independent release controlling agent, or the combination thereof, the formulation exhibited modified release of withanolides over a period of 6 to 12 hours, thus resulting into significant concentration of the active in the blood plasma over extended time. The formulation exhibits longer elimination half-life and thus results in modified release profile of the active over prolonged time.

The terminology 'pH independent release controlling agent' as used herein relates to the formulation component or carrier which is used for evenly dispersing and embedding Ashwagandha root powder enriched with withanolides. This component is found to be explicitly responsible for achieving modified release of the active by exhibiting longer elimination half-life; because of which the active remains in the blood plasma for longer time.

A pH independent release controlling agent is the formulation component or carrier whose solubility is independent of pH and hence its performance does not depend on the pH of the environment it encounters in the body. These agents may be either highly hydrophobic and non-swelling in nature or these can be also selected from the ones which are hydrophilic or swelling in nature. The release controlling agent may be preferably obtained from natural source, although the carriers may also be available from synthetic and semi-synthetic sources. These may include polymers, gums, cellulose derivatives, starch and starch derivatives, waxes, fatty acids, oils or the combination thereof.

The formulation, as described herein may be comprised of hydrophilic or hydrophobic pH independent release controlling agent or the combination thereof in various ratios, to achieve modified release of withanolides over a period of 6 to 12 hours, to maintain desired level of active in the body for extended period of time.

The terminology 'modified release' as used herein refers to the release of the active (withanolides or more specifically, total withanolides) from a formulation which is at a slower rate than from an immediate release formulation such as a conventional swallow tablet or capsule, so that the desired level of active is maintained in the body over 6 to 24 hours. The modified release formulation may exhibit slow, controlled, sustained, prolonged or extended release of the active. Preferably, the modified release formulations of the present invention are formulated such that release of the active is effectively modified in order to prolong or extend the elimination half-life of the active, so that it will not get cleared from the system at a rapid rate; but will maintain significant concentration in blood plasma over 6 to 24 hours.

The formulation comprising withanolides may be prepared by evenly dispersing and embedding the active in the matrix of one or more pH independent release controlling agents, which exhibits modified release of the active, resulting into significant concentration of total withanolides in blood plasma. The elimination half-life of the active is increased, thus the active become available in the body for longer time throughout the day.

As per one important embodiment, pH independent release controlling agent may be selected from the class of, but not limited to cellulose and cellulose derivatives, vinyl acetate-vinyl pyrrolidone polymers, starch and starch derivatives, gums, lipids, fats, fatty acids, waxes and the combination thereof.

As per one more embodiment of the invention, the formulation of the instant invention, may be comprised of at least one pH independent release controlling agent or the combination of more than one pH independent release controlling agent. The release controlling agent may be hydrophobic or hydrophilic in nature. The formulation as described herein, may be comprised of combination of hydrophobic and hydrophilic pH independent release controlling agents.

The pH independent release controlling agent may also be selected from, but not limited to, beeswax, candelilla wax, carnauba wax, spermaceti, paraffin wax, synthetic waxes and the combination thereof.

The pH independent release controlling agent may be selected from, but not limited to, saturated fatty acids having 12 to 28 carbons, such as stearic acid, fatty alcohols having from 16 to 44 carbons, cetyl alcohol, pegylated fatty acids, glycerol fatty acid esters, monoglycerides, diglycerides, triglycerides, derivatives of mono-diglycerides, glyceryl behenate, glyceryl monostearate, glyceryl palmitostearate, pegylated vegetable oils, partially hydrogenated oils of soy, cottonseed, palm, sunflower, castor oil, sorbitan esters, polyoxyethylene sorbitan esters, propylene glycol mono- or diesters, phospholipids, phosphatides, cerebrosides, gangliosides, cephalins, lipids, glycolipids, sulfatides, sugar esters, sugar ethers, sucrose esters, sterols, polyglycerol esters, glycerolipid, phosphatic acid, phosphatidylethanolamine, phosphatidylcholine, phosphatidylserine, phosphatidylinositol or other glycerophospholipids, ceramide, sphingolipid, sterol, fat-soluble vitamin, prenol, saccharolipid, polyketide, their salts and esters and the combination thereof.

As per one embodiment of the invention, pH independent release controlling agent may be selected from the group of cellulose derivatives such as hydroxypropylmethyl cellulose (HPMC), hydroxypropyl cellulose (HPC), ethylcellulose, carboxymethylcellulose (CMC), sodium CMC, potassium CMC, calcium CMC, methylcellulose, hydroxyethyl cellulose (HEC), vinyl pyrrolidone-vinyl acetate copolymer, polyethylene oxide, polyvinyl alcohol, starch, starch derivatives, modified starch, carbomer, gums like xanthan gum, guar gum, acacia, locust bean gum, alginates, or mixtures thereof.

As per further embodiment, the formulation may be comprised of at least one pH independent release controlling agent or the combination thereof, to achieve modified release formulation of the active. This is a component which is explicitly responsible for controlling or modifying release of withanolides from the formulation.

As per one embodiment of the invention, the formulation as described herein may comprise of about 10 to 90% by weight of pH independent release controlling agent. More preferably it may be comprised of about 30 to 70% by weight of release controlling agent.

As per one embodiment of the invention, modified release composition may be comprised of at least one excipient, which is acceptable in nutraceutical, pharmaceutical and cosmetic industry. The excipient may help as a processing aid in formulating the granules in desired dosage form intended for oral administration.

These are commonly used ingredient in industry, and may be selected from the group of, but not limited to, fillers, diluents, lubricants, binders, glidants, anti-caking agents, surfactants, channelizing agents, vehicles, buffers, acidifiers, alkalizers, complexing agents, gum bases, antioxidants, viscosity enhancers, solvents and the combination thereof.

Modified release formulation comprising withanolides as described herein, may be comprised of about 1 to 10% by weight of at least one excipient, which is selected from natural, semi-synthetic or synthetic sources.

The formulation may be comprised of diluents known in the art, but not limited to microcrystalline cellulose, silicified microcrystalline, powdered cellulose, microfine cellulose, corn starch, rice bran extract, mannitol, maltodextrin, calcium phosphate, dibasic calcium phosphate, tribasic calcium phosphate, calcium sulfate, or mixtures thereof. The diluents may also be selected from glucose, lactose, sucrose, dextrose, fructose, compressible sugar, or mixtures thereof.

The binders may be selected from the group of low viscosity cellulose derivatives such as hydroxypropylmethyl cellulose (HPMC), hydroxypropyl cellulose (HPC), ethylcellulose, carboxymethylcellulose (CMC), sodium CMC, potassium CMC, calcium CMC, methylcellulose, hydroxyethyl cellulose (HEC), microcrystalline cellulose; polyvinylpyrrolidone (PVP), vinyl pyrrolidone-vinyl acetate copolymer, polyvinyl alcohol, starch, gums like xanthan gum, guar gum, acacia, locust bean gum, alginates, or mixtures thereof.

The lubricants may be selected from magnesium stearate, calcium stearate, sodium benzoate, talc, or mixtures thereof.

The glidants may be selected from suitable glidants known in the art and commonly used in the industry, selected from the group of stearates, starch, talc and the derivatives.

The solvents may be selected from the group of aqueous or organic group, such as alcohol, isopropyl alcohol, higher alcohols, dicholoromethane, ethyl acetate, hexane and the combination thereof.

Therefore, according to important embodiment of the invention, provided herein is a modified release formulation comprising 2-10% of total withanolides, comprising (a) 20 to 70% of Ashwagandha root powder based on the total weight of the formulation, which is enriched with 8-20% of total withanolides, more particularly it is comprised of withanolide glycosides in the range of 3-15%, withanolide aglycones in the range of 2.5-8%, and withaferin-A in the range of 0.01-0.7%.

(b) 10 to 90% of at least one pH independent release controlling agent, preferably 30 to 70% of the pH independent release controlling agent based on the total weight of the modified release formulation, and (c) 1 to 10% by weight of at least one excipient, selected from the group of fillers, diluents, disintegrants, lubricants, binders, glidants, anti-caking agents, surfactants, channelizing agents, vehicles, buffers, complexing agents, gum bases, viscosity enhancers and the combination thereof.

These formulations are granular in nature, which can be used as such or can be converted in suitable dosage forms, such as compressible dosage forms, capsules or sachets, may exhibit modified release of the active throughout the day, thus resulting in extended elimination half-life and maintenance of significant concentration of withanolides in blood plasma over a period of 6 to 24 hours.

As per one more embodiment of the invention, the process for preparation of formulation comprising withanolides employs commonly available and easy to use industrial equipment.

According to important embodiment of the invention, the process for preparation of the modified release formulation may be comprised of evenly dispersing and embedding Ashwagandha root powder, enriched with withanolides, in pH independent release controlling agent using suitable equipment, by the way of fluidized-bed granulation, high-shear granulation, extrusion, or other suitable wet granulation processes. The granules may be also prepared by the process of melt granulation, melt extrusion, melt solidification and the combination thereof. Suitable parameters of temperature, revolutions and torque may be selected for carrying out melt granulation. The process may be carried out by varying the temperature in the range of 40 to 120° C. The molten form can be further processed to get granules suitable for converting into suitable compressible dosage form or can be filled in capsules or sachets.

The modified release formulation, as described herein, is subjected to dissolution study to understand release profile of active over extended time. The pharmacokinetics of the formulation, as described herein is also evaluated in animal model in comparison with immediate release formulation and the marketed reference products, following a single oral administration. The concentration of withanolides and other actives was determined to decide the t½ (half-life or elimination half-life) of individual formulations. The study is important to understand the need of modified release formulation over immediate release formulation, along with its comparison with marketed reference products.

The formulation is also subjected to evaluation of pharmacokinetic profile in healthy human volunteers to study plasma profile of the active after oral administration in comparison to marketed reference formulation. The formulation is also evaluated in standard lab rodents, which are subjected to conditions of chronic unpredictable stress (CUS), to check the efficacy in conditions of comorbid depression and anxiety. Efficacy of the formulation is also evaluated in healthy, adult, stressed subjects using The Cambridge Neuropsychological Test Automated Battery (CANTAB) over three months period. The modified release formulation of the invention was especially evaluated for its efficacy in improving the cognitive abilities and for reducing the psychological and physiological markers of stress.

The modified release profile of the formulation, providing the longer lasting effect of the active, may be suitable for application in stress management and for other cognitive benefits.

The following examples serve to illustrate specific embodiments of the invention claimed herein. All percentages are given in relation to the weight and all the temperatures are given in degree Celsius.

EXPERIMENTAL DATA

Example 1: Modified Release Formulation Comprising Withanolides

TABLE 1

Composition of granules comprising Ashwagandha root powder enriched in withanolides

| Ingredients | Formula 1 | Formula 2 | Formula 3 | Formula 4 | Formula 5 | Formula 6 |
|---|---|---|---|---|---|---|
| Ashwagandha Root powder | 47.62 | 40.16 | 40.165 | 40.16 | 40.16 | 44.64 |

TABLE 1-continued

| Composition of granules comprising Ashwagandha root powder enriched in withanolides | | | | | | |
|---|---|---|---|---|---|---|
| Ingredients | Formula 1 | Formula 2 | Formula 3 | Formula 4 | Formula 5 | Formula 6 |
| enriched with withanolides | | | | | | |
| Maltodextrin | 4.76 | — | — | — | — | — |
| Mannitol | 9.52 | — | — | — | — | — |
| Carnauba Wax | 35.72 | 54.22 | 58.23 | 50.20 | 50.20 | 44.64 |
| Stearic Acid | 0.00 | 4.02 | 0.00 | 0.00 | 8.03 | 8.93 |
| Silicon dioxide | 2.38 | 1.60 | 1.61 | 6.24 | 1.61 | 1.79 |
| Total | 100.00 | 100.00 | 100.00 | 100.00 | 100.00 | 100.00 |

Process for Formula 1

Ashwagandha root powder enriched with withanolides is mixed with maltodextrin, mannitol, carnauba wax and colloidal silicon dioxide. The mixture is sifted using vibratory sifter and the sifted material is mixed well in the blender. The blend is then fed into the twin screw processor with predetermined heating zones set at temperature of 40 to 120 degree celsius to obtain a mass which is screened through the mesh. The granules are then passed through a slow speed oscillating granulator, the granules which are retained on the oscillating granulator are then passed through multimill 1.5 mm screen, further the granules are sifted through 20 and 40 mesh and reprocessed in the twin screw processor.

Process for Formula 2 to Formula 6

Ashwagandha root powder enriched in withanolides is mixed with carnauba wax, stearic acid and colloidal silicon dioxide are sifted using vibratory sifter and the sifted material is mixed well in the blender. The blend is fed into the twin screw processor with predetermined heating zones set at temperature of 40 to 120 degree celsius to obtain a mass which is screened through the mesh. The granules are then passed through a slow speed oscillating granulator, the granules which are retained on the oscillating granulator are then passed through multimill 1.5 mm screen, further the granules are sifted through 20 and 40 mesh and reprocessed in the twin screw processor.

The dissolution of the compressed tablet formulation is carried out in 900 ml phosphate buffer of pH 6.8, contains 0.5% SLS using paddle at 100 rpm.

The active released during dissolution study was estimated using HPLC method, using pH 6.8 buffer and 100% Acetonitrile as mobile phase and standard column run conditions. The injection volume was 100 μL and the detection was carried out at 227 nm. As per USP method, 10 peaks of various withanolides were detected in the process of quantitative estimation.

TABLE 2

| Dissolution Profile of the modified release formulation comprising withanolides % Release in 900 mL Phosphate buffer pH 6.8 contains 0.5% SLS, 100 rpm, paddle | | | | | | |
|---|---|---|---|---|---|---|
| Time (hr) | Formula 1 | Formula 2 | Formula 3 | Formula 4 | Formula 5 | Formula 6 |
| 1 | 55 | 51 | 42 | 48 | 51 | 52 |
| 2 | 71 | 64 | 54 | 60 | 64 | 63 |
| 4 | 85 | 76 | 64 | 70 | 76 | 71 |

TABLE 2-continued

| Dissolution Profile of the modified release formulation comprising withanolides % Release in 900 mL Phosphate buffer pH 6.8 contains 0.5% SLS, 100 rpm, paddle | | | | | | |
|---|---|---|---|---|---|---|
| Time (hr) | Formula 1 | Formula 2 | Formula 3 | Formula 4 | Formula 5 | Formula 6 |
| 6 | 89 | 83 | 69 | 77 | 83 | 77 |
| 8 | 92 | 86 | 72 | 81 | 87 | 80 |

The formulation of the invention exhibits modified release of withanolides over a period of 6 to 12.

Example 2: Modified Release Formulation Comprising Withanolides

TABLE 3

| Composition of granules comprising Ashwagandha root powder enriched in withanolides | | | |
|---|---|---|---|
| Ingredients | Formula 7 | Formula 8 | Formula 9 |
| Ashwagandha Root powder enriched in withanolides | 20.48 | 31.06 | 30.96 |
| Maltodextrin | 30.12 | 7.76 | 7.74 |
| Mannitol | 36.75 | 50.31 | 51.39 |
| HPMC K4M | 12.05 | 9.32 | 3.10 |
| HPMC K100 LV | — | — | 3.10 |
| Magnesium stearate | 0.60 | 1.55 | 1.86 |
| Silicon dioxide | — | — | 1.86 |
| DCM | Qs | Qs | Qs |
| IPA | Qs | Qs | Qs |
| Total | 100.00 | 100.00 | 100.00 |

Process

Ashwagandha root powder, hydroxypropyl methyl cellulose, maltodextrin and mannitol along with other excipients are sifted using vibratory sifter and sifted material is mixed in the blender. The blend is granulated using sufficient amount of isopropyl alcohol and dichloromethane. The granules are dried in Fluidized bed dryer. The dried granules are milled and lubricated with magnesium stearate. The lubricated granules are compressed into tablets using 12×6 mm punches.

The dissolution of the compressed tablet formulation was carried out in 900 ml phosphate buffer of pH 6.8, contains 0.5% SLS using paddle at 100 rpm.

TABLE 4

| Dissolution profile of modified release tablet formulation % Release in 900 mL Phosphate buffer pH 6.8 contains 0.5% SLS, 100 rpm, paddle | | | |
|---|---|---|---|
| Time (hr) | Formula 7 | Formula 8 | Formula 9 |
| 1 | 15 | 18 | 21 |
| 2 | 25 | 27 | 35 |
| 4 | 42 | 49 | 60 |
| 6 | 65 | 69 | 83 |
| 8 | 91 | 84 | 101 |

The formulation of the invention exhibits modified release of withanolides over a period of 8 hours in sustained manner.

Example 3: Immediate Release Granules of Ashwagandha Extract Enriched in Withanolides

TABLE 5

| Composition for Immediate release granules | |
|---|---|
| Ingredients | Formula 10 |
| Ashwagandha Root powder enriched in withanolides | 75.76 |
| Maltodextrin | 7.58 |
| Mannitol | 15.15 |
| Silicon dioxide | 1.52 |
| Total | 100.00 |

Process

Ashwagandha root powder enriched in withanolides is mixed with maltodextrin and mannitol through a mesh using vibratory sifter and sifted material is mixed in the blender. The blended material is fed into Twin screw processor with predetermined heating zones set at temperature of 40 to 120 degree celsius. The resultant mass is cooled and passed through 60 mesh. The milled granules are lubricated using silicon dioxide.

The dissolution of the IR granules of Formula 10 is carried out in 900 ml phosphate buffer of pH 6.8, contains 0.5% SLS using paddle at 100 rpm.

TABLE 6

| Dissolution data of Ashwagandha IR Granules % Release in 900 mL Phosphate buffer pH 6.8 contains 0.5% SLS, 100 rpm, paddle | |
|---|---|
| Time (hr) | Formula 10 |
| 1 | 100% |

Example 4: Modified Release Formulation Comprising Withanolides

TABLE 7

| Composition of SR granules comprising Ashwagandha root powder enriched in withanolides and the dissolution data | | | | |
|---|---|---|---|---|
| Ingredients (% w/w) | Formula 11 | Formula 12 | Formula 13 | Formula 14 |
| Ashwagandha Root powder enriched in withanolides | 30 | 30 | 70 | 50 |
| Carnauba Wax | — | — | 30 | — |
| Cetylalcohol | 70 | — | — | — |
| Glyceryl monostearate | — | 70 | — | — |
| Glyceryl behenate | — | — | — | 50 |
| Total (%) | 100.00 | 100.00 | 100.00 | 100.00 |
| % Release in 500 mL Phosphate buffer pH 6.8 contains 0.5% SLS, 100 rpm, paddle | | | | |
| Time (hr) | Formula 11 | Formula 12 | Formula 13 | Formula 14 |
| 1 hr | 34 | 40 | 53 | 48 |
| 2 hr | 52 | 56 | 68 | 58 |
| 4 hr | 73 | 73 | 80 | 75 |
| 6 hr | 84 | 87 | 85 | 81 |
| 8 hr | 96 | 99 | 95 | 88 |
| Particle size | 840 microns to 1000 microns | | | |

Process for Preparation: Ashwagandha root powder enriched in withanolides is mixed with at least one pH independent release controlling agent such as carnauba wax, cetyl alcohol, glyceryl monostearate or glyceryl behenate are sifted using vibratory sifter and the sifted material is mixed well in the blender. The blend is fed into the twin screw processor with predetermined heating zones set at temperature of 40 to 120 degree celsius to obtain a mass which is screened through the mesh to get the granules.

The dissolution of the granules is carried out in 500 ml phosphate buffer of pH 6.8, contains 0.5% SLS using paddle at 100 rpm.

Example 5: Modified Release Formulation Comprising Withanolides

TABLE 8

Composition of modified release tablet formulation comprising Ashwagandha root powder enriched in withanolides and the dissolution data

| | Formula 15 | Formula 16 |
|---|---|---|
| Ingredients % w/w | | |
| Dosage Form | Modified release Tablets | Modified release Tablets |
| Ashwagandha modified release granules (Formula 13) | — | 82 |
| Ashwagandha root powder enriched in withanolides | 62 | — |
| HPMC K100 LV | 15 | 16.5 |
| Maltodextrin | 8 | — |
| Mannitol | 13 | — |
| Silicon Dioxide | 1 | 0.77 |
| Magnesium Stearate | 1 | 0.77 |
| IPA | q.s. | — |
| MDC | q.s. | — |
| Total | 100 | 100 |
| Time (hr) | | |
| 1 hr | 13 | 12 |
| 2 hr | 28 | 23 |
| 4 hr | 59 | 42 |
| 6 hr | 81 | 72 |
| 8 hr | 101 | 91 |

Process for Formula 15

Ashwagandha root powder, hydroxypropyl methyl cellulose, maltodextrin and mannitol along with other excipients are sifted using vibratory sifter and sifted material is mixed in the blender. The blend is granulated using sufficient amount of isopropyl alcohol and dichloromethane. The granules are dried in fluidized bed dryer. The dried granules are milled and lubricated with magnesium stearate. The lubricated granules are compressed into tablets using 12×6 mm punches.

Process for Formula 16

Modified release granules obtained in the form of Formula 13 were mixed and blended with hydroxypropyl methyl cellulose along with other excipients are sifted using vibratory sifter and sifted material is mixed in the blender. The blend is granulated using sufficient amount of isopropyl alcohol and dichloromethane. The granules are dried in fluidized bed dryer. The dried granules are milled and lubricated with magnesium stearate. The lubricated granules are compressed into tablets using 12×6 mm punches.

Example 6: Identification of Withanolides from Ashwagandha Root Powder

Withanolide components (withanolide glycosides, withanolide aglycones and withaferin A) from *Withania somnifera* root powder were identified in the form of 20 different withanolides as follows:

Withanolide glycosides were identified as Withanoside IX, Withanoside VIII, Withanoside IV, Withanoside VI, Withanoside V, Withanoside III, Withanoside II, Physagulin D Withanolide aglycones were identified as Withaferin A3-Hydroxy, Withaferin A Sulphate, Withanolide A Sulphate, Withanolide LN, 2,3-dehydrosominiferacin, 12-deoxy withastramonolide, Withanolide A, Withanolide D, Withanone, 7,27-dihydroxy-1-oxo-with a-2,5,25-trienolide and Withanolide B Withaferin A was also identified as one of the withanolides in Ashwagandha root powder.

Ashwagandha root powder is enriched with 8-20% of total withanolides, more particularly it is comprised of withanolide glycosides in the range of 3-15%, withanolide aglycones in the range of 2.5-8%, and withaferin-A in the range of 0.01-0.7%.

Example 7: Comparative Pharmacokinetic Evaluation of the Modified Release Formulation (Formula 2) and the Immediate Release Formulation (Formula 10) in Rats Pharmacokinetics of withanolides following a single oral administration of Ashwagandha immediate release (IR) formulation (Formula 10), Ashwagandha modified release formulation (Formula 2), and two marketed comparator products was evaluated in Male Sprague Dawley Rats following a single oral dose of 50 mg/kg.

4 actives were analyzed viz., Withanoside IV, Withanoside V, 12-deoxywithastramonolide and withanolide A. Of these, the half-life ($t\frac{1}{2}$) was calculable only for 12-deoxywithastramonolide.

IR formulation showed $t\frac{1}{2}$ of 1.08 hours, while modified release formulation of the invention (Formula 2) had $t\frac{1}{2}$ of 4.75 hours. The marketed reference product had $t\frac{1}{2}$ of 0.47 hours.

For total withanolides measured (Withanoside IV and V, Withanolide A, 12-deoxy withastromonolide), IR formulation showed $t\frac{1}{2}$ of 1.33 hours, while modified release formulation had $t\frac{1}{2}$ of 11.87 hours.

For the marketed reference products, the $t\frac{1}{2}$ of total withanolides was not estimable.

The study indicates that there is a significantly high difference in the elimination half-life between the immediate release formulation (Formula 10) and the modified release formulation of the invention, suggesting quick elimination of the withanolides from the immediate release formulation, in comparison with the modified release formulation. This necessitates the need of the modified release formulation comprising withanolides, which would exhibit prolonged elimination half-life, thus making the active available in the body for extended time.

Example 8: Pharmacokinetic Evaluation of Formula 2

In the open label, randomized, balanced, two treatment, two sequence, two period, crossover, single oral comparative pharmacokinetic study conducted on 14 healthy human subjects, based on pharmacokinetic and statistical analysis, after administration of single dose, the Test Product (T) [Modified release formulation of the present invention-Test product] 300 mg (containing 15 mg withanolides) (2×15 mg)] when compared with the Reference marketed Product (R) [containing 15 mg withanolides) (2×15 mg)].

The findings are as follows:

For the active withanolide A, the elimination half-life (t %/2) for the test product (Modified release formulation of the invention) was 7.4561 hours as compared to 0.7406 hours for the reference product.

For 12-deoxy withastramonolide, the t %2 for the test product was 7.5317 hours as compared to 2.2909 hours for the reference product.

For total withanolides, the t %/2 for the test product was 7.0708 hours as compared to 2.2789 hours for the reference product.

The modified release profile of the formulation of present invention is well established through comparative pharmacokinetic study conducted against the reference product, for the 2 actives tested, i.e., 12-deoxy withastramonolide and withanolide A as well as total withanolides.

The formulation as described herein exhibits higher relative absorption as well as superior relative bioavailability as compared to the marketed reference product. The formulation also exhibits longer elimination half-life showing the modified release profile of the actives over longer time-period for the total withanolides. The modified release profile of the formulation would be useful for providing significant concentration of the active in blood plasma over extended time of 6 to 24 hours.

Example 9: Evaluation of Efficacy of Modified Release Formulation on Stressed Animal Models Using Behavioural Assays The objective of the study was to evaluate the efficacy of modified release Ashwagandha formulation on chronic unpredictable stress (CUS) induced comorbid depression and anxiety in Sprague Dawley Rats.

Animals were housed in a ratio of 3-4 animals per cage and maintained under standard environmental conditions of temperature, relative humidity and 12 h light/dark cycle except on the day of inversion of light/dark cycle (for induction of CUS) throughout the study duration. The formulation of the invention was used as a test item, along with two marketed comparator Ashwagandha extract formulations, Escitalopram was used as a reference standard and 0.5% carboxymethylcellulose sodium (CMC-Na) was used as a vehicle. Marketed test formulations as well as reference standard was added in required amount of 0.5% carboxymethylcellulose sodium to get the final suspension or solution respectively, which can be administered to the rats.

Animals in G1 and G2 groups were administered with 0.5% CMC-Na orally 10 mL/kg/body weight. The modified release formulation of the invention was filled in mini-capsules and administered orally to G3 group. Test items (Marketed comparator formulation 1 and 2-Ashwagandha extracts) were administered orally to G4 and G5 groups at maximum dose volume of 10 mL/kg/body weight. Animals in G6 received escitalopram (reference standard) at the dose of 20 mg/kg/body weight by oral route. All animals were dosed with respective vehicle/test item/reference standard once daily till the final day (day 1-35).

All animals except, the animals in normal control group (G1) underwent the various predefined paradigms of chronic unpredictable stress for 35 days, in which the animals were either exposed to noise, inversion of light and dark cycle, cold water swim, wet bedding, restrained or deprived from food. Various behavioral tests were conducted and recorded at definite interval. Blood samples were collected on the last day and all animals were euthanized and brain, thymus, adrenals were collected and weighed. Brain tissues from all animals (G1-G6) were collected and stored till further analysis.

Various tests such as Open field test (OFT), Elevated plus maze (EPM), Forced swim test (FST), Morris water maze (MWM), Acquisition Trial, Probe Trial were carried out. Throughout the study duration animals which received test items were free from adverse clinical signs. This indicates that the test items are well tolerated at the tested doses. Administration of the formulation of the invention (G3) modulated the stress induced anxiety by correcting the CUS induced alterations. It also resulted in increase in the distance travelled and speed in open field in comparison with CUS control group. Treatment with modified release formulation prevented the rise in serum corticosterone in G3 animals.

Based on these observations, we conclude that modified release Ashwagandha formulation protected the rats from CUS induced anxiety like behavior, depression and cognitive impairment. The study indicates that administration of modified release formulation comprising withanolides, protected the rats from CUS induced anxiety like behavioral abnormalities by reducing the restlessness, elevating the mood and improving the memory and retention of memory. In addition, administration of the formulation also protected the rats from CUS induced elevation of serum corticosterone levels in rats. Further, the formulation is well tolerated by the rats as the animals were free from adverse clinical signs. The overall outcome of this study highlights the beneficial effects of the formulation, as described herein, in combating with stress induced anxiety and depression.

Example 10: Evaluation of Modified Release Formulation in Healthy, Adult, Stressed Subjects The efficacy and safety of modified release Ashwagandha formulation on cognitive functions was evaluated in healthy, adult and stressed subjects through a prospective double-blind, randomized, multi-centre, two-arm, placebo-controlled trial. The formulation was also checked for its safety and tolerability.

Male or female healthy, adult, human subjects aged between 20-55 years with BMI 18 to 29 kg/m2, who perceived themselves to be under mild to moderate stress were selected for the study. These subjects were confirmed to be cognitively sound, with no cognitive impairment. 130 subjects were randomized and were allocated for specific treatments as per the randomization schedule, using formulation of the invention (test formulation-capsule) and the placebo (look alike inert capsule formulation). The protocol also complied with ICH-Good Clinical Practice (GCP) and the Helsinki Declaration Standards, as well as Schedule Y (amended version 2005) and Indian Council of Medical Research codes. Subjects received either one of the test or placebo product once daily after breakfast over a 3 months treatment period.

The change in cognition function from baseline to the end of the study period was measured by CANTAB connect (The Cambridge Neuropsychological Test Automated Battery) which included various tests such as—Motor screening test (MOT), Paired Associates Learning (PAL), Reaction Time (RTI), Rapid visual information processing (RVP) and Spatial working memory (SWM). The secondary endpoints for evaluation of cognitive function included Perceived Stress Scale-10 (PSS-10) score, Serum Cortisol level (9-11 am), Oxford Happiness Questionnaire (OHQ), The Pittsburgh Sleep Quality Index (PSQI) and Serum Brain Derived Neurotropic Factor (BDNF).

Key parameters of PAL modules showed that recalling memory was significantly improved and the total error rate in recalling patterns were statistically significantly decreased in the test group as compared to the placebo group. The primary objective of the study i.e. improvement in memory is achieved with the test product. In the sustained attention measured by the RVP modules, the measure of signal detection was improved substantially with the test product as compared to placebo. The reduction latency was found to be higher with test treatment when compared to placebo. Stress level was significantly decreased in test group compared to placebo as evidenced by a statistically significant reduction in serum cortisol level and PSS score. There was a statistically significant increase in OHQ score in the test group compared to the placebo group, which shows that the product increased the well-being in the study subjects taking the test product. The PSQI score was significantly reduced in the test group compared to placebo group, showing improvement in the quality and pattern of sleep in the test group.

The trial clearly demonstrated that subjects administered with the modified release formulation of the invention, showed increased abilities to perform better in three domains of cognitive skills such as visual memory and working and sustained attention. Also, the formulation of the invention was able to improve the subjects' happiness level demonstrating psychological wellbeing, along with sleep quality. The formulation, as described herein, indicates improvement in cognition by reducing the stress levels along with a clear improvement in memory which is an additional benefit as compared to traditional anxiolytics which can cause sedation and hamper mental abilities.

In conclusion, this study demonstrates that modified release formulation comprising withanolides, has significantly improved cognitive abilities, reduced psychological and physiological markers of stress, and improved mental well-being as well as improvement in memory. The study has also demonstrated the safety of the test formulation throughout the treatment period.

The formulation comprising ashwagandha root powder, as described herein was administered as a once-daily modified release capsule. This formulation has the potential for better bioavailability of withanolides for extended time, as evidenced through the pharmacokinetic evaluation described in Example 7. Single daily dose of the formulation, as described herein is expected to increase subject's compliance and by maintaining blood level of active constituents for extended time, it offers health benefits in terms of improved cognition level, memory and quality of sleep. The modified release formulation comprising withanolides is evaluated for the first time for its efficacy in the form of objective measurement of cognitive improvement and found to be beneficial in healthy adult stressed subjects.

We claim:

1. A modified release formulation comprising Ashwagandha Root powder enriched with withanolides comprising 2% to 10% of total withanolides, based on the total weight of the modified release formulation, embedded in a matrix of a pH independent release controlling agent, wherein (i) the formulation releases no more than 80% of the withanolides within 4 hours, (ii) the formulation releases more than 75% of the withanolides over a period of 6 hours to 12 hours, (iii) the formulation is in an oral form, and (iv) the pH independent release controlling agent is selected from the group consisting of carnauba wax, stearic acid, hydroxypropyl methyl cellulose, vinyl pyrrolidone-vinyl acetate copolymer, polyvinyl alcohol, cetyl alcohol, glyceryl monostearate, glyceryl behenate, and mixtures thereof.

2. The modified release formulation as claimed in claim 1, comprising about 2% to 10% of total withanolides, based on the total weight of the modified release formulation, embedded in a matrix of about 10% to 90% of the pH independent release controlling agent, based on the total weight of the modified release formulation.

3. The modified release formulation as claimed in 2, comprising about 20% to 70% by weight of root powder of *Withania somnifera*, based on the total weight of the modified release formulation, and about 30% to 70% by weight of the pH independent release controlling agent, based on the total weight of the modified release formulation.

4. The modified release formulation as claimed in claim 1, further comprising about 1% to 10% by weight of at least one excipient, which is acceptable in pharmaceutical, nutraceutical and food industry, and acts as a processing aid for preparation of granular composition, based on the total weight of the modified release formulation.

5. A process for making the modified release formulation of claim 1, comprising:

a. mixing Ashwagandha root powder, enriched in withanolides, with the pH independent release controlling agent and the excipient by using a suitable blender to obtain a mixture, b. subjecting the mixture obtained in step (a) in suitable equipment having predetermined heating zones set at a temperature of 40° C. to 120° C. Celsius to obtain a mass, c. screening the mass obtained in step (b) through a mesh and sifting equipment to obtain granules, and d. converting the granules obtained in step (c) into a dosage form.

6. The modified release formulation of claim 1, which is for management of stress, improvement in cognitive abilities along with improvement in memory, sleep, and overall mental well-being of the human.

7. The modified release formulation of claim 1, wherein the pH independent release controlling agent is carnauba wax and stearic acid.

8. The process of claim 1, wherein the oral form is selected from the group consisting of a capsule, tablet, and sachet.

* * * * *